(12) United States Patent
Stihl et al.

(10) Patent No.: US 8,317,796 B2
(45) Date of Patent: Nov. 27, 2012

(54) REDUCTION TOOL

(75) Inventors: Pascal Stihl, Grenchen (CH); Helmut Rutschmann, Klettgau (DE)

(73) Assignee: Synthes USA, LLC, West Chester, PA (US)

(*) Notice: Subject to any disclaimer, the term of this patent is extended or adjusted under 35 U.S.C. 154(b) by 49 days.

(21) Appl. No.: 13/062,848

(22) PCT Filed: Sep. 11, 2009

(86) PCT No.: PCT/US2009/056706
§ 371 (c)(1),
(2), (4) Date: Mar. 8, 2011

(87) PCT Pub. No.: WO2010/030916
PCT Pub. Date: Mar. 18, 2010

(65) Prior Publication Data
US 2011/0166606 A1    Jul. 7, 2011

Related U.S. Application Data

(60) Provisional application No. 61/096,612, filed on Sep. 12, 2008.

(51) Int. Cl.
*A61B 17/88* (2006.01)
(52) U.S. Cl. ....................... 606/86 A; 606/279
(58) Field of Classification Search .......... 606/246, 606/264, 265, 270, 279, 301, 99, 104, 86 A; 403/362; 411/393
See application file for complete search history.

(56) References Cited

U.S. PATENT DOCUMENTS

2005/0149036 A1* 7/2005 Varieur et al. ............... 606/86
2008/0177269 A1   7/2008 Seelig

FOREIGN PATENT DOCUMENTS

| WO | WO 98/52482   | 11/1998 |
| WO | WO 2006/116437 | 11/2006 |
| WO | WO 2009/015100 | 1/2009  |
| WO | WO 2010/030916 | 3/2010  |

OTHER PUBLICATIONS

International Patent Application No. PCT/US2009/056706: International Search Report dated Mar. 26, 2010, 4 pages.

* cited by examiner

*Primary Examiner* — Alvin Stewart
*Assistant Examiner* — David Comstock
(74) *Attorney, Agent, or Firm* — Woodcock Washburn LLP

(57) ABSTRACT

A reduction tool for use in posterior spinal fixation to facilitate insertion of a longitudinal spinal rod into a rod-receiving channel formed in a bone fixation element. The reduction tool preferably includes an outer tube sized and configured to transversely receive the spinal rod therethrough, the outer tube being operatively coupled to the bone fixation element, an inner tube operatively coupled to a locking cap and slidably disposed within the outer tube, and a rotatable sleeve for rotatably advancing the inner tube with respect to the outer tube to advance the spinal rod into the rod-receiving channel formed in the bone fixation element and to couple the locking cap to the bone fixation element to thereby secure the rod within the bone fixation element.

18 Claims, 14 Drawing Sheets

REDUCTION TOOL

CROSS-REFERENCE TO RELATED APPLICATIONS

This application is the National Stage of International Application No. PCT/US2009/056706, filed Sep. 11, 2009, which claims the benefit of U.S. Provisional Application No. 61/096,612, filed Sep. 12, 2008, the disclosures of which are incorporated herein by reference in their entireties for all purposes.

FIELD OF THE INVENTION

The present invention relates generally to orthopedics. More specifically, the present invention relates to a reduction tool and associated method for facilitating insertion of a longitudinal spinal rod into a rod-receiving channel formed in a bone fixation element.

BACKGROUND OF THE INVENTION

Spinal fixation systems which are used to correct spinal deformities and treat spinal degenerations generally include a plurality of bone fixation elements anchored in, for example, the pedicle of adjacent vertebrae. The bone fixation elements are interconnected to one another by, for example, one or more elongated spinal rods. In order to access the spinal area for implantation of these spinal fixation systems and their individual components, open approach surgical techniques have traditionally been employed. These open procedures generally involve large skin incisions and extensive tissue retraction and resection, all which may result in considerable post-operative pain and prolonged recovery time.

More recently, surgeons have used minimally invasive techniques to reduce the post-operative effects of spinal fixation procedures. A paraspinal approach is one form of minimally invasive technique and involves muscle splitting or muscle sparing in order to gain access to the posterior elements of the spine. Such a technique minimizes trauma to tissues adjacent the spine. Unlike open procedures where muscles and other soft tissue are cut, split, stripped and dissected, the paraspinal approach involves separation or splitting of the muscles along their fibers.

Implanting a spinal rod fixation system generally involves at least two steps: (i) placing bone fixation elements into the spine and (ii) inserting a rod between the bone fixation elements. Bone fixation elements generally include a screw portion and a body portion. The screw portion is inserted into the spine and the body portion generally includes a rod-receiving channel for receiving and securing the spinal rod. The rod may be inserted through an incision in the skin, which may be separate and distinct from the incision through which the bone fixation element(s) is placed. Alternatively, the rod may be inserted through the same incision as the bone fixation element(s).

It is desirable to have a minimally invasive bone fixation element and rod introduction system which minimizes trauma to the body, provides for simplified and time saving instrumentation for rod reduction, enables a rod to be readily connected to multiple bone fixation elements anchored at varying depths in the body, is generally simple to use, enhances direct visualization of the rod as the rod is being inserted into the bone fixation elements and facilitates securement of the rod to the bone fixation elements.

BRIEF SUMMARY OF THE INVENTION

The present invention is directed to a reduction tool and associated method of use for posterior spinal fixation to facilitate insertion of a longitudinal spinal rod into a rod-receiving channel formed in a bone fixation element. The reduction tool preferably includes an outer tube, an inner tube and a rotatable sleeve. The outer tube is preferably sized and configured to transversely receive the spinal rod therethrough and is operatively coupled to the bone fixation element. The inner tube is preferably operatively coupled to a locking cap and is slidably disposed within the outer tube. The rotatable sleeve is preferably operatively associated with the inner tube and the outer tube such that rotation of the sleeve moves the inner tube with respect to the outer tube thereby advancing the spinal rod into the rod-receiving channel formed in the bone fixation element and thereby coupling the locking cap to the bone fixation element to secure the rod to the bone fixation element.

In one exemplary embodiment, the reduction tool includes an outer tube, an inner tube and a rotatable sleeve. The outer tube preferably includes a proximal end, a distal end and a lumen defining an inner surface, the lumen extending from the proximal end to the distal end. The distal end including an engagement feature for engaging a body portion of a bone fixation element. The inner surface including a plurality of threads. The inner tube preferably includes a proximal end, a distal end and a lumen extending from the proximal end to the distal end, the inner tube being slidably disposed within the lumen formed in the outer tube. The distal end of the inner tube including an engagement member for engaging a locking cap. The rotatable sleeve preferably including a proximal end, a distal end and a lumen extending from the proximal end to the distal end, the rotatable sleeve being rotatably coupled to the proximal end of the inner tube. The rotatable sleeve further including a plurality of external threads for threadably engaging the threads formed on the inner surface of the outer tube such that rotation of the sleeve advances the inner tube with respect to the outer tube and hence downwardly and non-rotationally forces the locking cap and the elongated spinal rod into engagement with the body portion of the bone fixation element to provisionally lock the locking cap to the body portion of the bone fixation element and thus secure the spinal rod within the rod-receiving channel formed in the body portion of the bone fixation element.

The outer tube preferably also includes a pair of diametrically opposed slots extending from the distal end of the outer tube such that when the outer tube is engaged to the body portion of the bone fixation element, the diametrically opposed slots align with the rod-receiving channel formed in the bone fixation element. The diametrically opposed slots being sized and configured to enable the elongated spinal rod to transversely extend therethrough. The outer tube preferably also includes a pair of diametrically opposed guide slots extending from the proximal end of the outer tube for receiving one or more pins protruding from an outer surface of the inner tube. The guide slots being substantially aligned with the diametrically opposed slots extending from the distal end of the outer tube. The outer tube preferably also includes a pivot point located longitudinally between each of the diametrically opposed slots extending from the distal end of the outer tube and each of the diametrically opposed guide slots extending from the proximal end of the outer tube so that the distal end of the outer tube can be spread apart to facilitate engagement with the body portion of the bone fixation element. The outer tube may also include one or more guide recesses formed in the inner surface of the outer tube, the guide recesses extending from the proximal end of the outer tube. The guide recesses slidably receiving the engagement feature formed on the inner tube.

In one exemplary method of use, the surgeon preferably forms an incision at a desired location in a patient to access the patient's bones, for example, to access adjacent vertebral bodies. Next, the surgeon implants two or more bone fixation elements into the patient's bones through the incision, for example, the surgeon may insert one bone fixation element into each of the adjacent vertebral bodies. The outer tube of one of the reduction tools is then coupled to each of the pre-implanted bone fixation elements. The spinal rod is then transversely inserted through each of the outer tubes. The surgeon then inserts one of the inner tubes with the locking cap coupled thereto into each of the lumens formed in the outer tubes until the threads formed on the rotatable sleeves engage the corresponding threads formed on the outer tubes. The surgeon then rotates the rotatable sleeve to further advance the inner tubes with respect to the outer tubes until the spinal rod is seated within the rod-receiving channels formed in the body portions of the bone fixation elements and the locking caps engage the body portions of the bone fixation elements.

BRIEF DESCRIPTION OF THE SEVERAL VIEWS OF THE DRAWINGS

The foregoing summary, as well as the following detailed description of the preferred embodiments of the application, will be better understood when read in conjunction with the appended drawings. For the purposes of illustrating the reduction tool and associated method of use, there is shown in the drawings a preferred embodiment. It should be understood, however, that the application is not limited to the precise arrangements and instrumentalities shown. In the drawings:

FIG. 8A illustrates a detailed view of an exemplary, partial embodiment of a locking cap engagement feature formed on the distal end of the inner tube for coupling the locking cap to the inner tube;

DETAILED DESCRIPTION OF THE INVENTION

Figure 1:
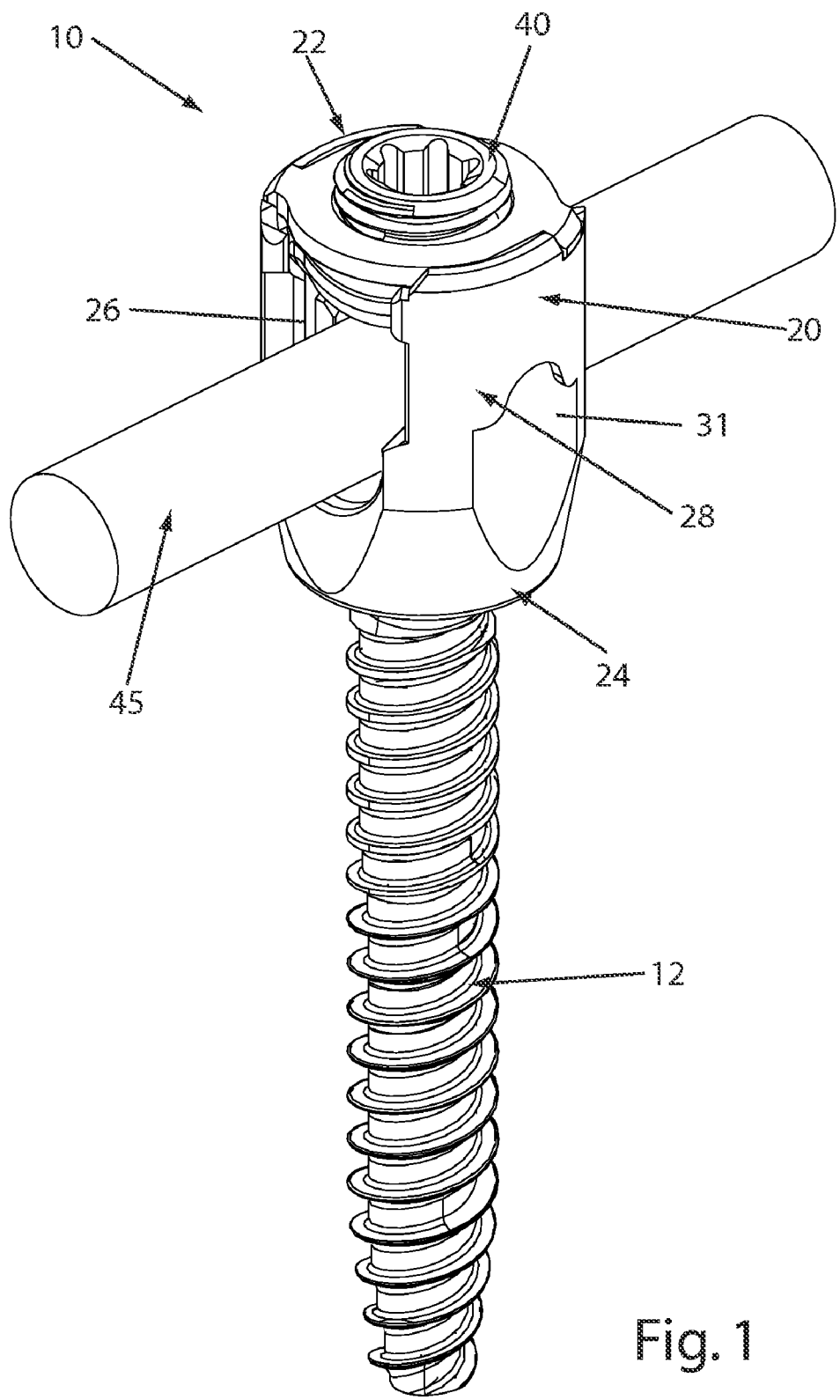
FIG. 1 is a perspective view of an exemplary, prior art bone fixation element.

Certain terminology is used in the following description for convenience only and is not limiting. The words "right", "left", "lower" and "upper" designate directions in the drawings to which reference is made. The words "inwardly" or "distally" and "outwardly" or "proximally" refer to directions toward and away from, respectively, the geometric center of the reduction tool and related parts thereof. The words, "anterior", "posterior", "superior", "inferior" and related words and/or phrases designate preferred positions and orientations in the human body to which reference is made and are not meant to be limiting. The terminology includes the above-listed words, derivatives thereof and words of similar import.

An exemplary embodiment of the invention will now be described with reference to the drawings. In general, such embodiment relates to a reduction tool 100, by way of non-limiting example, a reduction tool 100 for use in posterior spinal fixation to facilitate insertion of a longitudinal spinal rod 45 into a rod-receiving channel 26 formed in a bone fixation element 10. The invention may have other applications and uses and should not be limited to the structure or use described and illustrated.

As will be described in greater detail below, the reduction tool 100 preferably includes an outer tube 110 sized and configured to transversely receive the spinal rod 45 therethrough, the outer tube 110 being operatively coupled to the bone fixation element 10, an inner tube 150 operatively coupled to a locking cap 40 and slidably disposed within the outer tube 110, and a rotatable sleeve 180 for rotatably advancing the inner tube 150 with respect to the outer tube 110 to advance the spinal rod 45 into the rod-receiving channel 26 formed in the bone fixation element 10 and to couple the locking cap 40 to the bone fixation element 10 to secure the rod 45 to the bone fixation element 10.

While the reduction tool 100 will be described as and may generally be used in the spine (for example, in the lumbar, thoracic or cervical regions), those skilled in the art will appreciate that the reduction tool 100 may be used for fixation of other parts of the body such as, for example, joints, long bones or bones in the hand, face, feet, extremities, cranium, etc.

As previously mentioned and as will be described in greater detail below, the reduction tool 100 may be used to facilitate insertion of the longitudinal spinal rod 45 into the rod-receiving channel 26 formed in the bone fixation element 10. It should be understood that the spinal rod 45 may include, but not limited to, a solid rod, a non-solid rod, a flexible or dynamic rod, etc. It should be understood that the reduction tool 100 is not limited in use to any particular type of spinal rod 45.

In addition, as generally understood by one of ordinary skill in the art, it should be understood that bone fixation element 10 is used generally and may include, but are not limited to, poly-axial or mono-axial pedicle screws, hooks (both mono-axial and poly-axial) including pedicle hooks, transverse process hooks, sublaminar hook, or other fasteners, clamps or implants.

Figure 2:
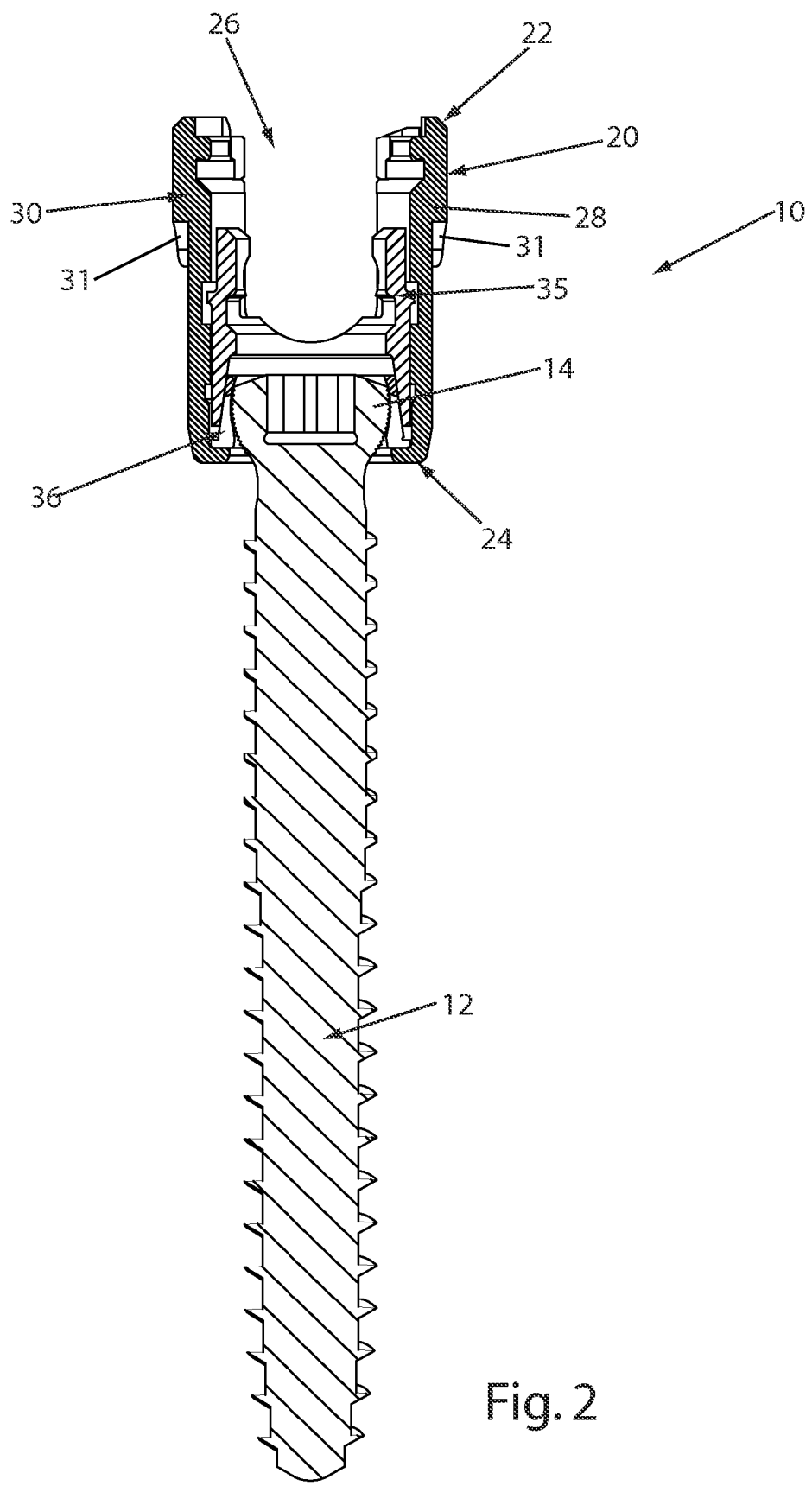
FIG. 2 is a cross-sectional view of the bone fixation element shown in FIG. 1.

Referring to FIGS. 1 and 2, an exemplary embodiment of a bone fixation element 10 is shown. The bone fixation element 10 may include a bone anchor 12 (shown as a bone screw) having an enlarged, spherically-shaped head portion 14, a body portion 20 (shown as a top loading body portion) having an upper end 22, a lower end 24, a rod-receiving channel 26 (shown as a top loading U-shaped rod-receiving channel) defining a pair of spaced apart arms 28, 30, a sleeve 35 and a collet 36 slidably disposed within the body portion 20, at least a portion of the collet 36 being slidably disposed within the sleeve 35, and a locking cap 40 such as, for example, a set screw or a partial turn closure cap such as, for example, a quarter-turn closure cap or cam lock. In use, the enlarged head portion 14 of the bone anchor 12 may be separate from and be disposed within the lower end 24 of the body portion 20 so that the bone anchor 12 can poly-axial rotate with respect to the body portion 20. Alternatively, the bone anchor 12 may be formed integral with the body portion 20 to form a monolithic structure which is sometimes referred to as a mono-axial pedicle screw or hook.

Once the spinal rod 45 is inserted into the rod-receiving channel 26, the surgeon can secure the position of the rod 45 with respect to the body portion 20 and the position of the bone anchor 12 with respect to the body portion 20 by, for example, rotating the locking cap 40. Rotation of the locking cap 40 preferably causes the locking cap 40 to exert a downward force onto the spinal rod 45, which is received within the rod-receiving channel 26, which, in turn, causes the rod 45 to exert a downward force onto the sleeve 35 with causes the sleeve 35 to move with respect to the collet 36, which in turn causes the collet 36 to compress around the enlarged head portion 14 of the bone anchor 12 thereby securing the position of the bone anchor 12 with respect to the body portion 20. In addition, rotation of the locking cap 40 may cause the spinal rod 45 to be sandwiched in-between the locking cap 40 and the sleeve 35 thereby securing the position of the rod 45 with respect to the body portion 20. It should be understood however that the reduction tool 100 is not limited in use to any particular type of bone fixation element 10.

Exemplary embodiments of bone fixation elements 10 include those described in International Patent Application No. PCT/US2008/070670, filed on Jul. 21, 2008, entitled "Polyaxial Bone Fixation Element", International Patent Application No. PCT/US2006/015692, filed on Apr. 25, 2006, entitled "Bone Anchor with Locking Cap and Method of Spinal Fixation", and International Patent Application No. PCT/CH1997/00236, filed on Jun. 16, 1997, entitled "Device for Connecting a Longitudinal Support with a Pedicle Screw", the contents of which are hereby incorporated by reference in their entirety. It should be understood however that the present invention is not limited in use to any particular type of bone fixation element 10.

Figure 3:
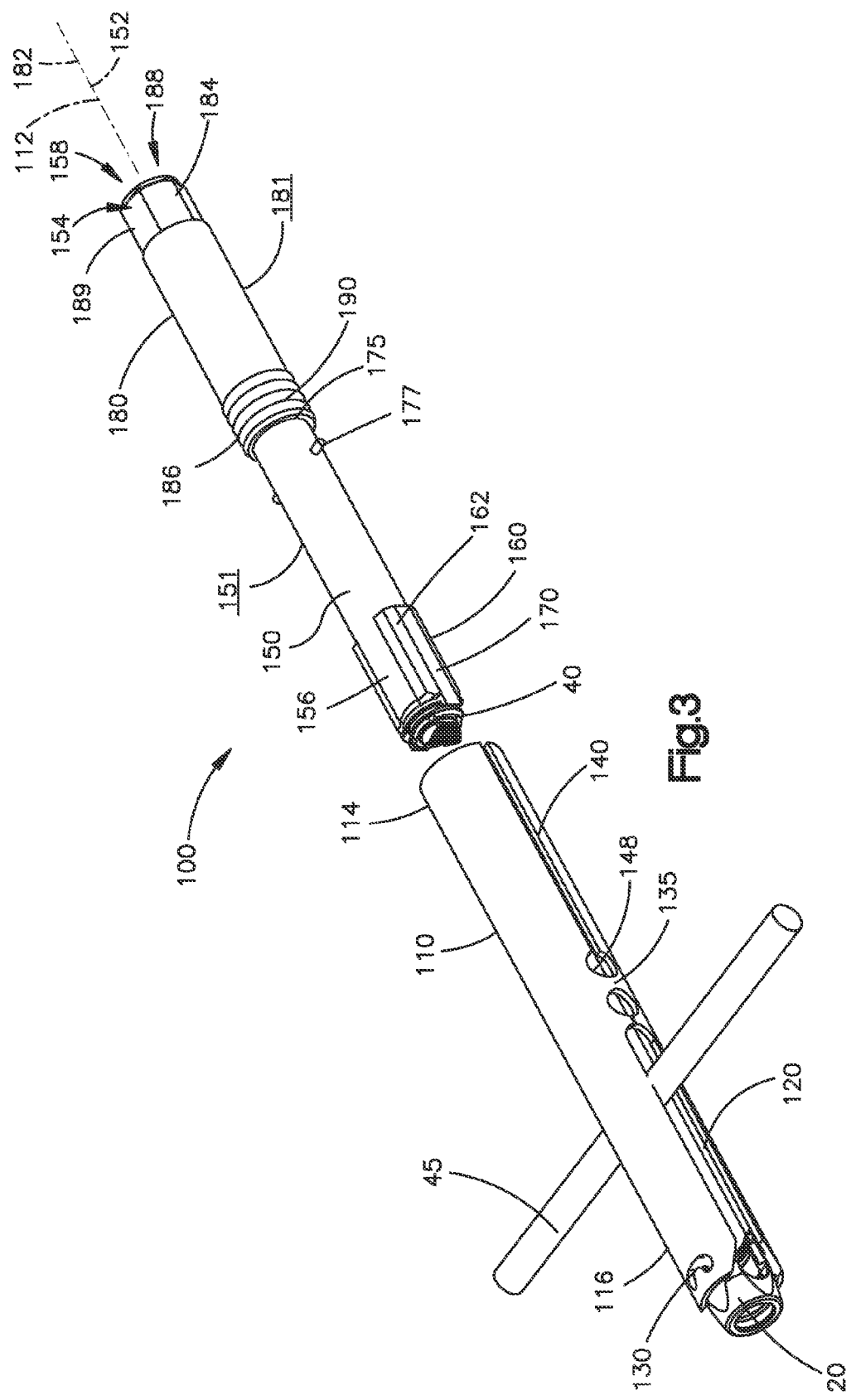
FIG. 3 illustrates an exploded, perspective view of a preferred embodiment of a reduction tool in accordance with the present invention, the reduction tool including an outer tube, an inner tube and a rotatable sleeve, the outer tube being operatively coupled to a body portion of the bone fixation element shown in FIG. 1 and illustrating an unreduced spinal rod extending transversely through the outer tube.
Figure 4:
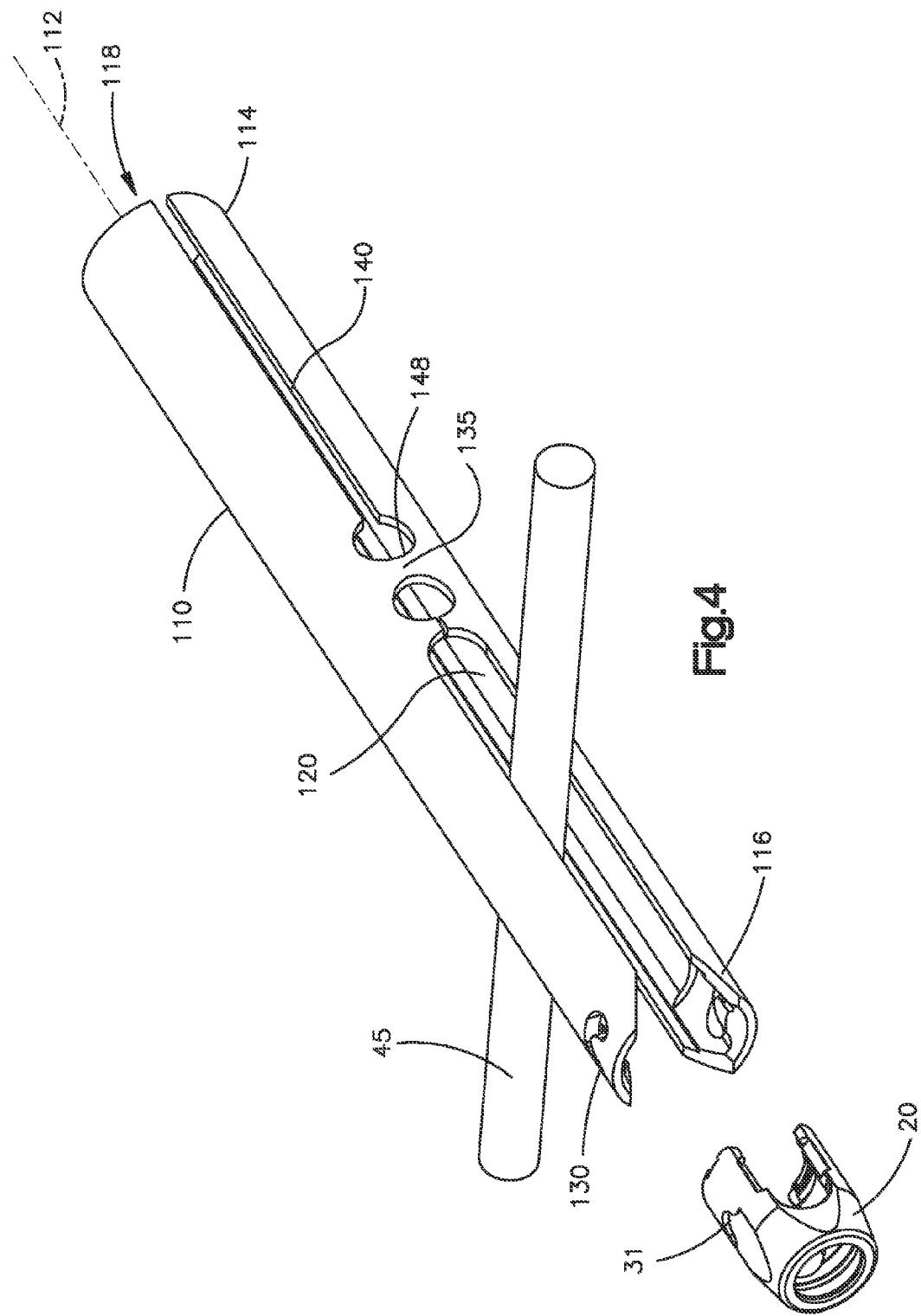
FIG. 4 illustrates a perspective view of the outer tube shown in FIG. 3, the outer tube being decoupled from the body portion of the bone fixation element shown in FIG. 1 and including an unreduced spinal rod extending therethrough.
Figure 5:
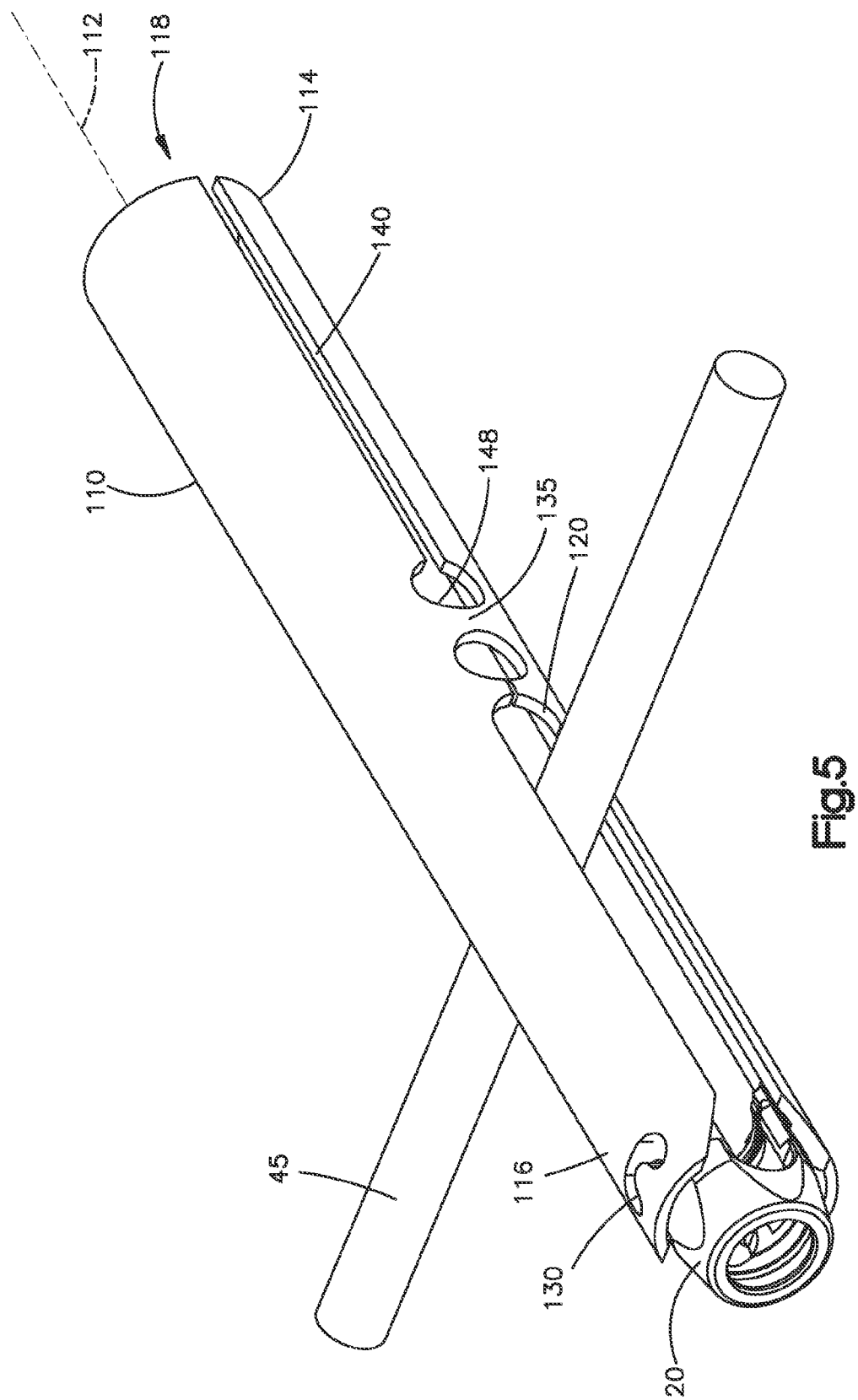
FIG. 5 illustrates an alternate perspective view of the outer tube shown in FIG. 3, the outer tube being operatively coupled to the body portion of the bone fixation element shown in FIG. 1 and including an unreduced spinal rod extending therethrough.
Figure 6:
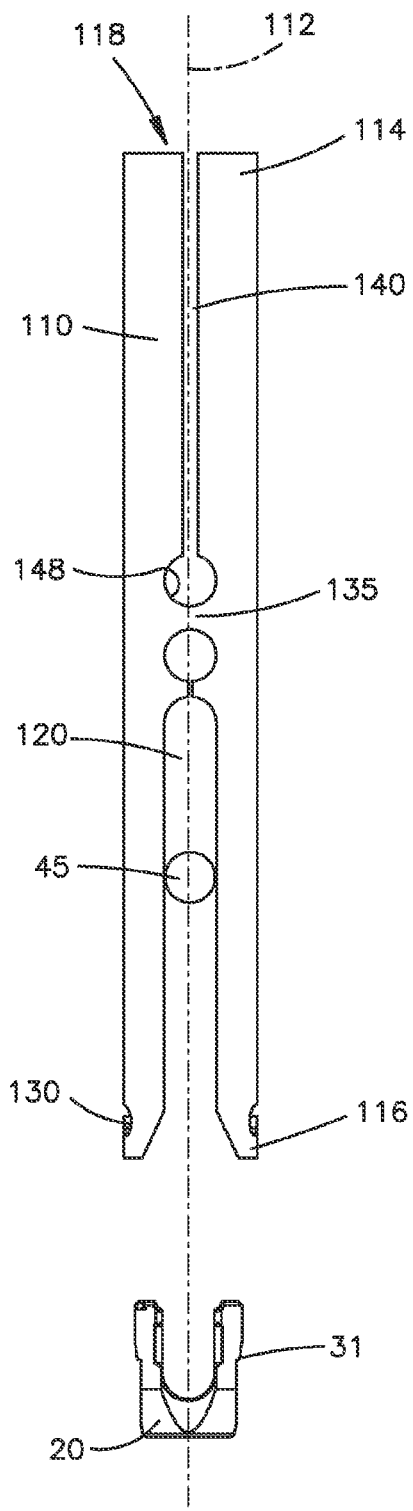
FIG. 6 illustrates a side view of the outer tube shown in FIG. 3, the outer tube being decoupled from the body portion of the bone fixation element shown in FIG. 1 and including an unreduced spinal rod extending therethrough.
Figure 7:
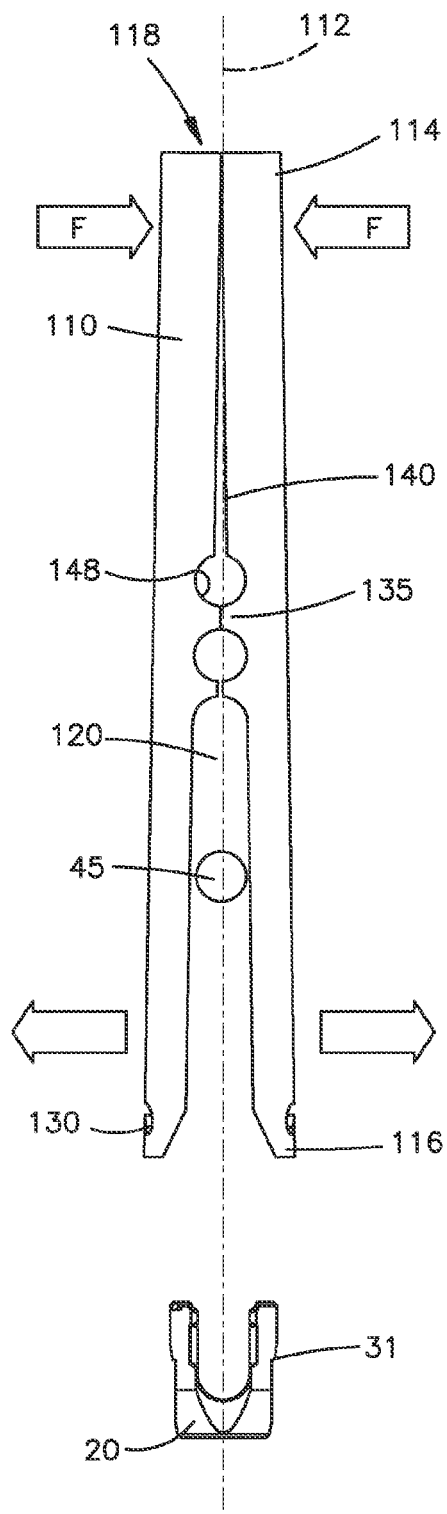
FIG. 7 illustrates an alternate side view of the outer tube shown in FIG. 3, the outer tube being decoupled from the body portion of the bone fixation element shown in FIG. 1 and including an unreduced spinal rod extending therethrough, a proximal end of the outer tube being subjected to a force to expand a distal end of the outer tube.

Referring to FIG. 3, the reduction tool 100 includes an outer tube 110, an inner tube 150 and a rotatable sleeve 180. The outer tube 110 is operably coupled to the inner tube 150, which is operatively coupled to the rotatable sleeve 180. More preferably, at least a portion of the inner tube 150 is slidably received within the outer tube 110 and at least a portion of the inner tube 150 is disposed within the rotatable sleeve 180 so that the rotatable sleeve 180 can operatively engage the outer tube 110 after the inner tube 150 has been advanced a sufficient distance into the outer tube 150, as will be described in greater detail below.

Referring to FIGS. 3-7, the outer tube 110 preferably includes a longitudinal axis 112, a proximal end 114, a distal end 116 and a lumen 118 extending from the proximal end 114 to the distal end 116. The outer tube 110 preferably also includes a pair of diametrically opposed slots 120 extending from the distal end 116 of the outer tube 110 such that when the outer tube 110 is coupled to the body portion 20 of the bone fixation element 10, the diametrically opposed slots 120 align with the rod-receiving channel 26 formed in the bone fixation element 10 so that the spinal rod 45 can pass from the reduction tool 100 into the rod-receiving channel 26. As shown, the diametrically opposed slots 120 preferably extend approximately halfway between the distal end 116 and the proximal end 114.

The distal end 116 of the outer tube 110 preferably includes an engagement feature 130 for engaging a corresponding feature 31 formed on the outer surface of the body portion 20 of the bone fixation element 10. The engagement feature 130 can be any feature or element now or hereafter known in the art including, for example, threads, etc. Preferably however the outer tube 110 includes one or more projections for mating with one or more shoulders or recesses formed on the outer surface of the body portion 20, or vice versa.

The outer tube 110 preferably also includes a pivot point 135. More preferably, the outer tube 110 includes a pivot point 135 disposed at approximately a halfway point between the proximal and distal ends 114, 116 of the outer tube 110. The pivot point 135 is preferably located between the diametrically opposed slots 120 extending from the distal end 116 of the outer tube 110 and the diametrically opposed guide slots 140 extending from the proximal end 114 of the outer tube 110, as will be described in greater detail below. The pivot points 135 serve as a fulcrum about which an inwardly applied force to the proximal end 114 of the outer tube 110 across the guide slots 140 is transmitted as an outwardly spreading force to the distal end 116 of the outer tube 110 across the diametrically opposed slots 120 so that the engagement features 130 formed on the distal end 116 of the outer tube 110 can surround and engage the corresponding features 31 disposed on the outer surface of the body portion 20 of the bone fixation element 10. That is, in use, the surgeon preferably applies an inwardly directed force to the proximal end 114 of the outer tube 110 thereby at least partially closing the guide slots 140 extending from the proximal end 114 of the outer tube 110. The inwardly directed force is transmitted through the pivot points 135 or fulcrum resulting in an outwardly spreading force to the distal end 116 of the outer tube 110 so that the distal end 116 of the outer tube 110 can surround and engage the body portion 20 of the bone fixation element 10. More specifically, to allow the distal end 116 of the outer tube 110 to spread open so that the engagement features 130 (e.g., projections, etc.) formed on the distal end 116 of the outer tube 110 can engage the features 31 (e.g., recess, etc.) formed on the outer surface of the body portion 20 on the bone fixation element 10. Removal of the inwardly directed force at the proximal end 114 of the outer tube 110 preferably results in the automatic closing of the distal end 116 of the outer tube 110 and the engagement of the engagement features 130 formed on the outer tube 110 to the features 31 formed on the bone fixation element 10.

It should be noted that it is not necessary for an inwardly directed force to be applied to the proximal end 114 of the outer tube 110 for the outer tube 110 to engage the body portion 20; instead, the distal end 116 of the outer tube 110 can be sized and configured to snap over the body portion 20 as a result of the flexibility allowed by the diametrically opposed slots 120 and the engagement features 130 can couple to features 31 as a result thereof.

Figure 8:
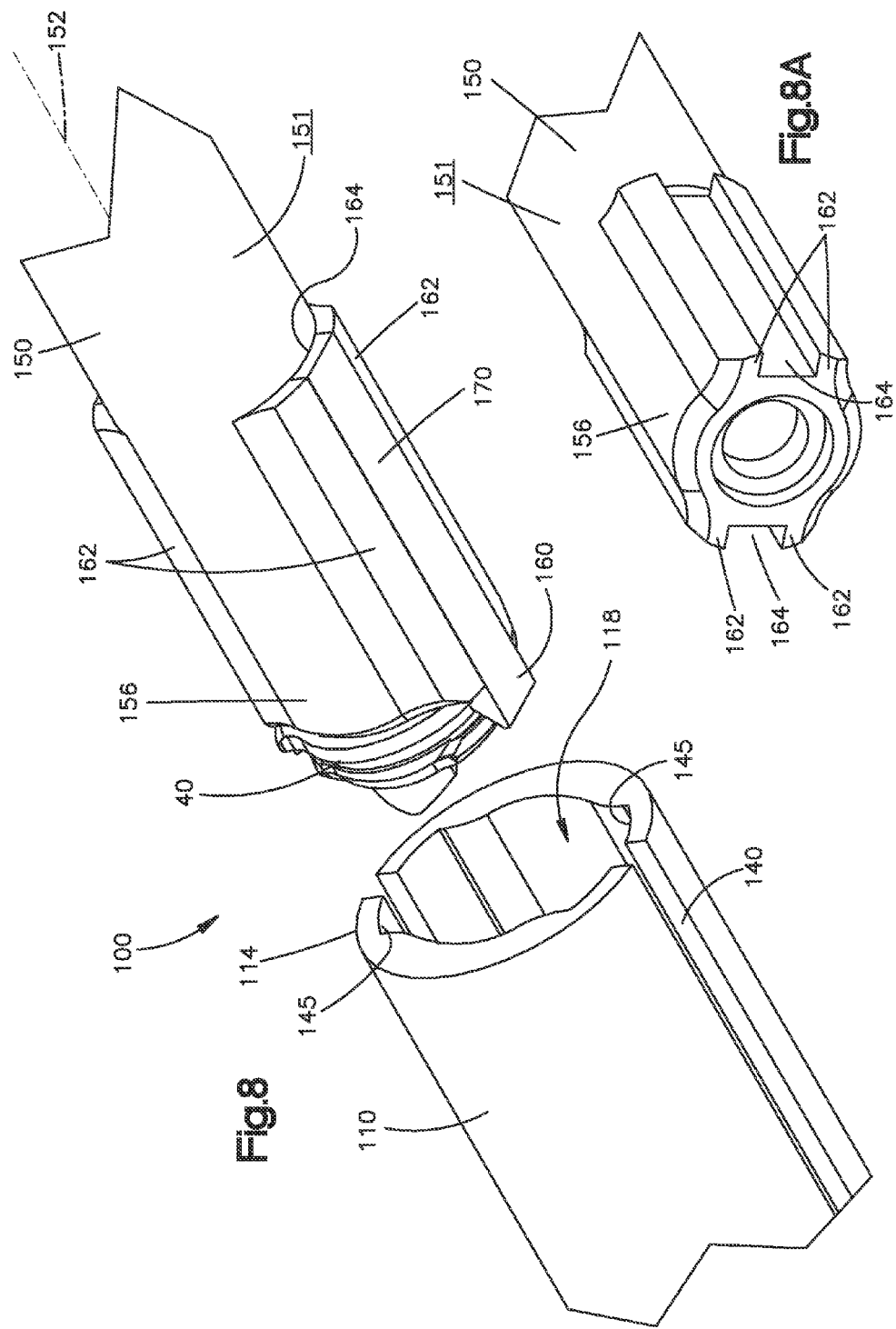
FIG. 8 illustrates a detailed, perspective view of a proximal end of the outer tube decoupled from a distal end of the inner tube.
Figure 9:
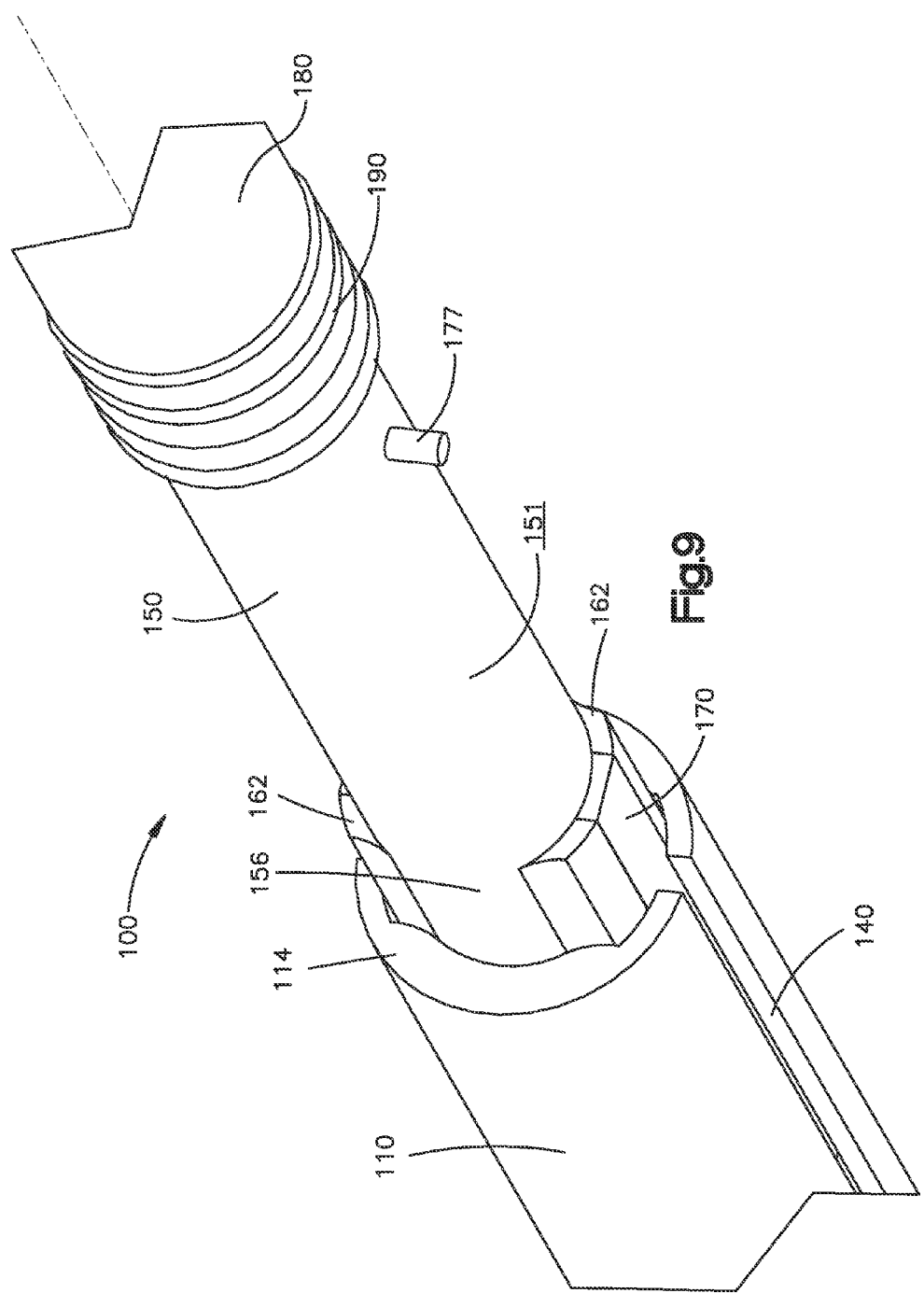
FIG. 9 illustrates a detailed, perspective view of the distal end of the inner tube being slidably received within a lumen formed in the proximal end of the outer tube.

Referring to FIGS. 8 and 9, the outer tube 110 preferably also includes one or more guide recesses 145 formed in an inner surface of the outer tube 110. More preferably, the outer tube 110 includes a pair of diametrically opposed guide recesses 145. The guide recesses 145 preferably extend from the proximal end 114 of the outer tube 110 parallel to the longitudinal axis 112. The guide recesses 145 are sized and configured to mate with one or more protrusions 162 formed on an outer surface 151 of the inner tube 150 and with one or more cantilever engagement members 170, as will be described in greater detail below.

In addition, referring to FIGS. 3-9 and as previously mentioned, the outer tube 110 preferably also includes one or more guide slots 140, and more preferably a pair of diametrically opposed guide slots 140 disposed in the outer surface of the outer tube 110 and extending from the proximal end 114 along the longitudinal axis 112 for receiving and guiding one or more pins 177 protruding from an outer surface 151 of the inner tube 150, as will be described in greater detail below. The diametrically opposed guide slots 140 are preferably aligned with the pair of diametrically opposed slots 120 but separated therefrom via the pivot pins 135 or fulcrum on either side of the outer tube 110. That is, a longitudinal axis of each guide slot 140 is preferably parallel to and collinear with a longitudinal axis of each slot 120. Furthermore, the pair of diametrically opposed guide slots 140 are preferably aligned with and overlapping with the pair of diametrically opposed guide recesses 145.

The outer tube 110 also preferably includes a pin stop 148 at the distal end of the guide slots 140, which is preferably located near or proximal to the halfway point between the proximal and distal ends 114, 116. The pin stop 148 extends transversely through the outer tube 110 and is sized and configured to contact the one or more pins 177 protruding from the outer surface 151 of the inner tube 150 to prevent over advancement of the inner tube 150 with respect to the outer tube 110, as will be described in greater detail below. As shown, the pin stop 148 may be nothing more than the pivot pin 135 so that over advancement of the inner tube 150 with respect to the outer tube 110 is prevented by the pin stop 148 contacting the pivot pin 135. Alternatively, the pin stop 148 may be a surface separate and distinct from the pivot pin 135.

Referring to FIGS. 3, 8, 8a and 9, the inner tube 150 preferably includes a longitudinal axis 152, a proximal end 154, a distal end 156 and a lumen 158 extending from the proximal end 154 to the distal end 156. The inner tube 150 preferably also includes one or more engagement features 160 at or near the distal end 156 of the inner tube 150 for engaging the locking cap 40 of the bone fixation element 10. The engagement feature 160 may be any feature now or hereafter known for coupling the locking cap 40 to the distal end 156 of the inner tube 150. For example, the distal end 156 of the inner tube 150 may include a pair of protrusions 162 formed on an outer surface 151 of the inner tube 150. The protrusions 162 incorporating and/or separated by a channel 164 for engaging a cantilever engagement member 170. The cantilever engagement members 170 are preferably sized and configured to extend beyond the distal end 156 of the inner tube 150 and to snap lock over the locking cap 40 by aligning the cantilever engagement member 170 over the locking cap 40 and applying a downward force. That is, an interior surface of the cantilever engagement member 170 may be sized and configured to snap lock over an external surface of the locking cap 40 for securely coupling the locking cap 40 to the distal end 156 of the inner tube 150. In use and as previously mentioned, the protrusions 162 and cantilever engagement member 170 are slidably received within the guide recesses 145 formed in the inner surface of the outer tube 110.

Figure 10:
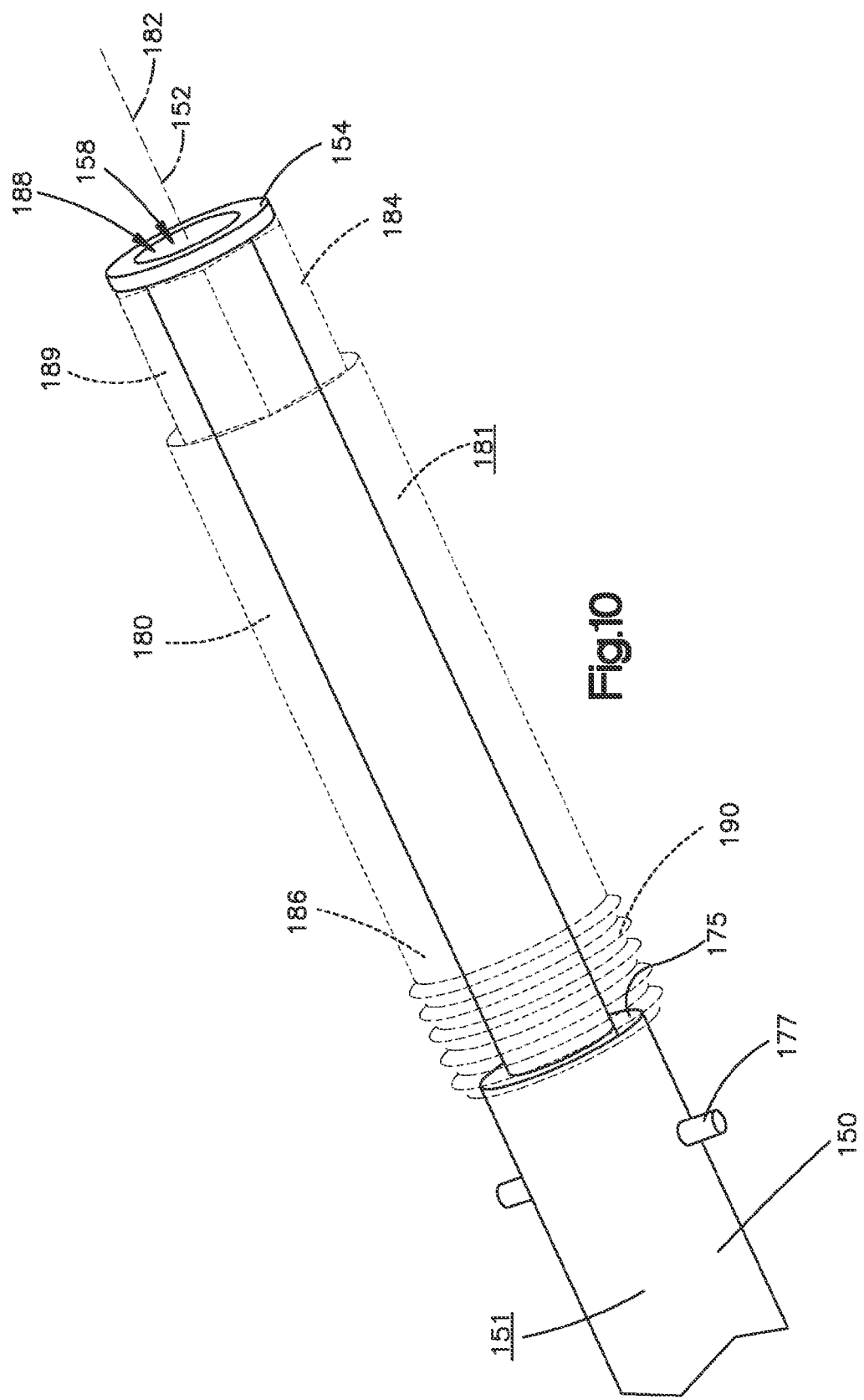
FIG. 10 illustrates a side view of the rotatable sleeve coupled to the proximal end of the inner tube.
Figure 11:
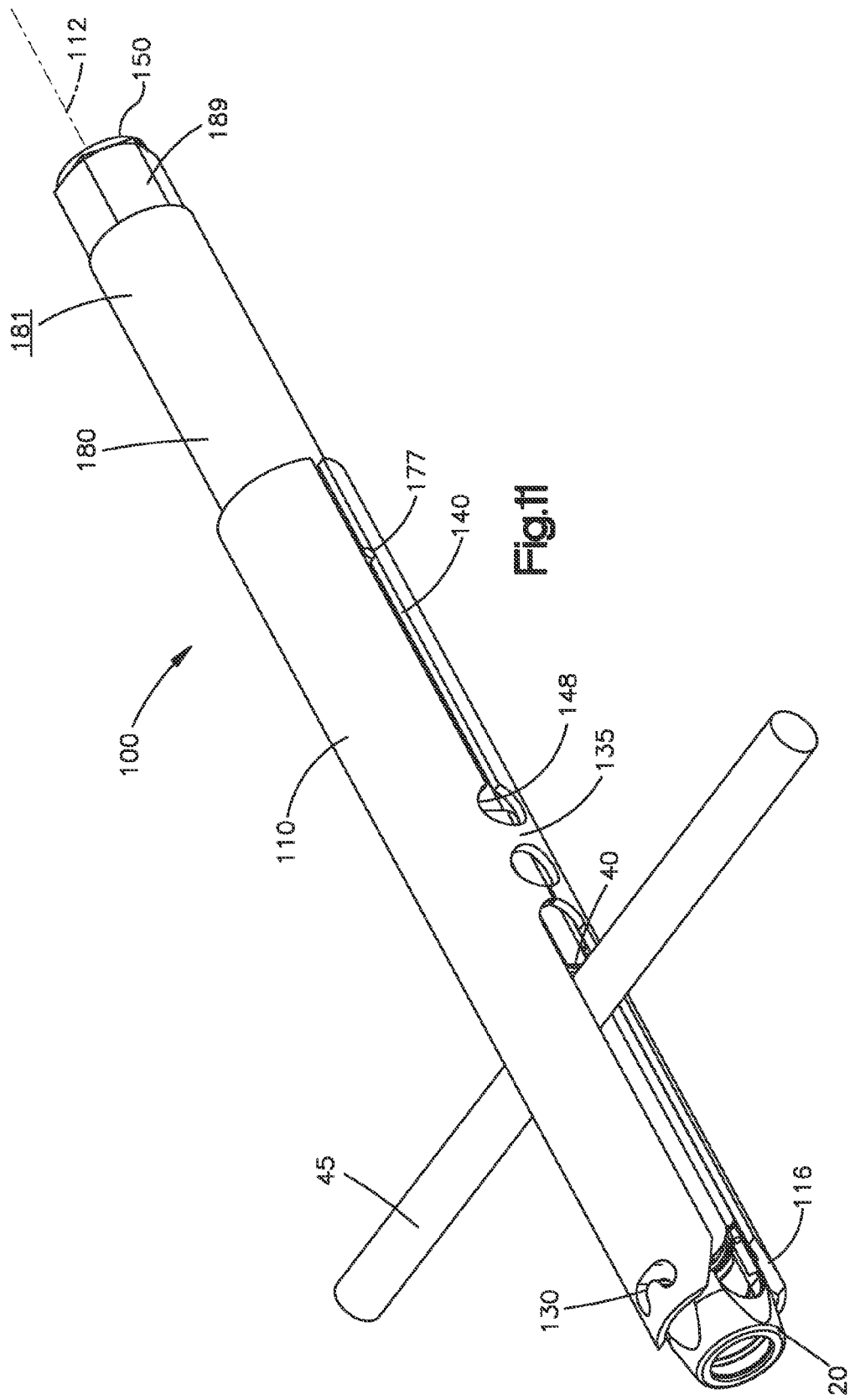
FIG. 11 illustrates a perspective view of the reduction tool shown in FIG. 3 during reduction of the spinal rod, the reduction tool being coupled to the body portion of the bone fixation element shown in FIG. 1 and including a spinal rod extending transversely therethrough.
Figure 12:
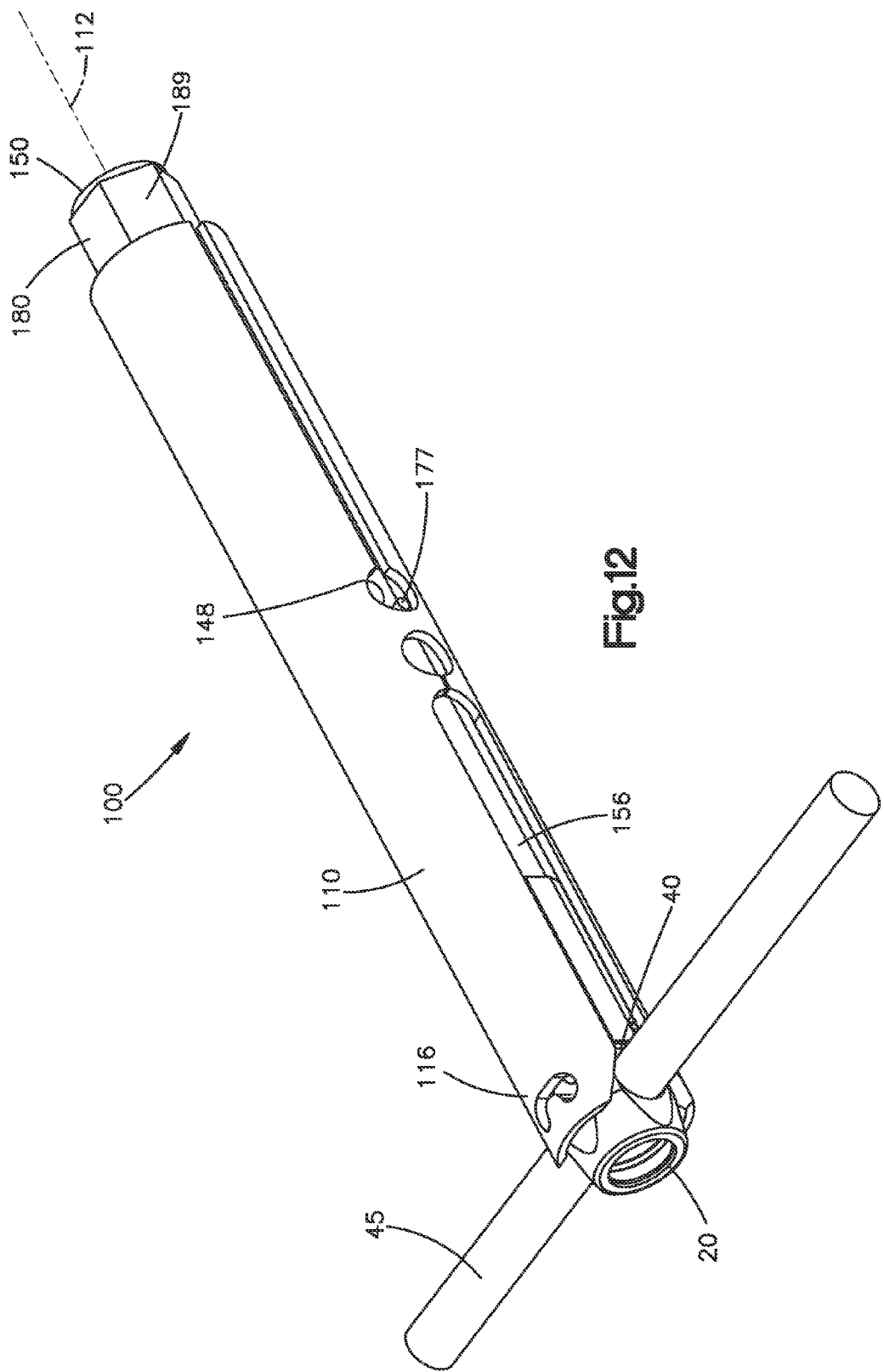
FIG. 12 illustrates a perspective view of the reduction tool shown in FIG. 3 after reduction of the spinal rod into the rod-receiving channel formed in the bone fixation element and provisional locking of the locking cap to the body portion.
Figure 13:
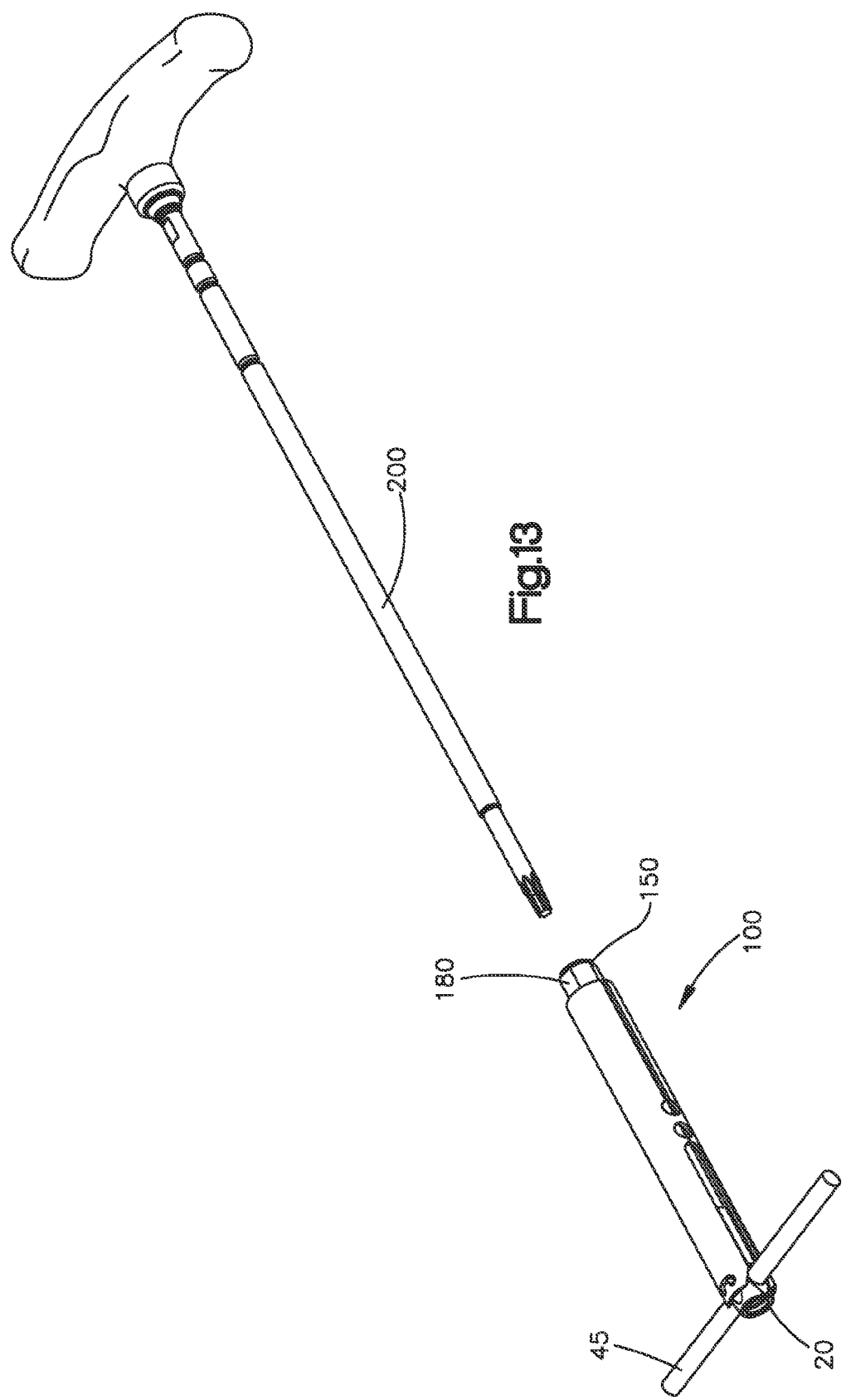
FIG. 13 illustrates a perspective view of the reduction tool shown in FIG. 12 in combination with an exemplary embodiment of a drive tool.
Figure 14:
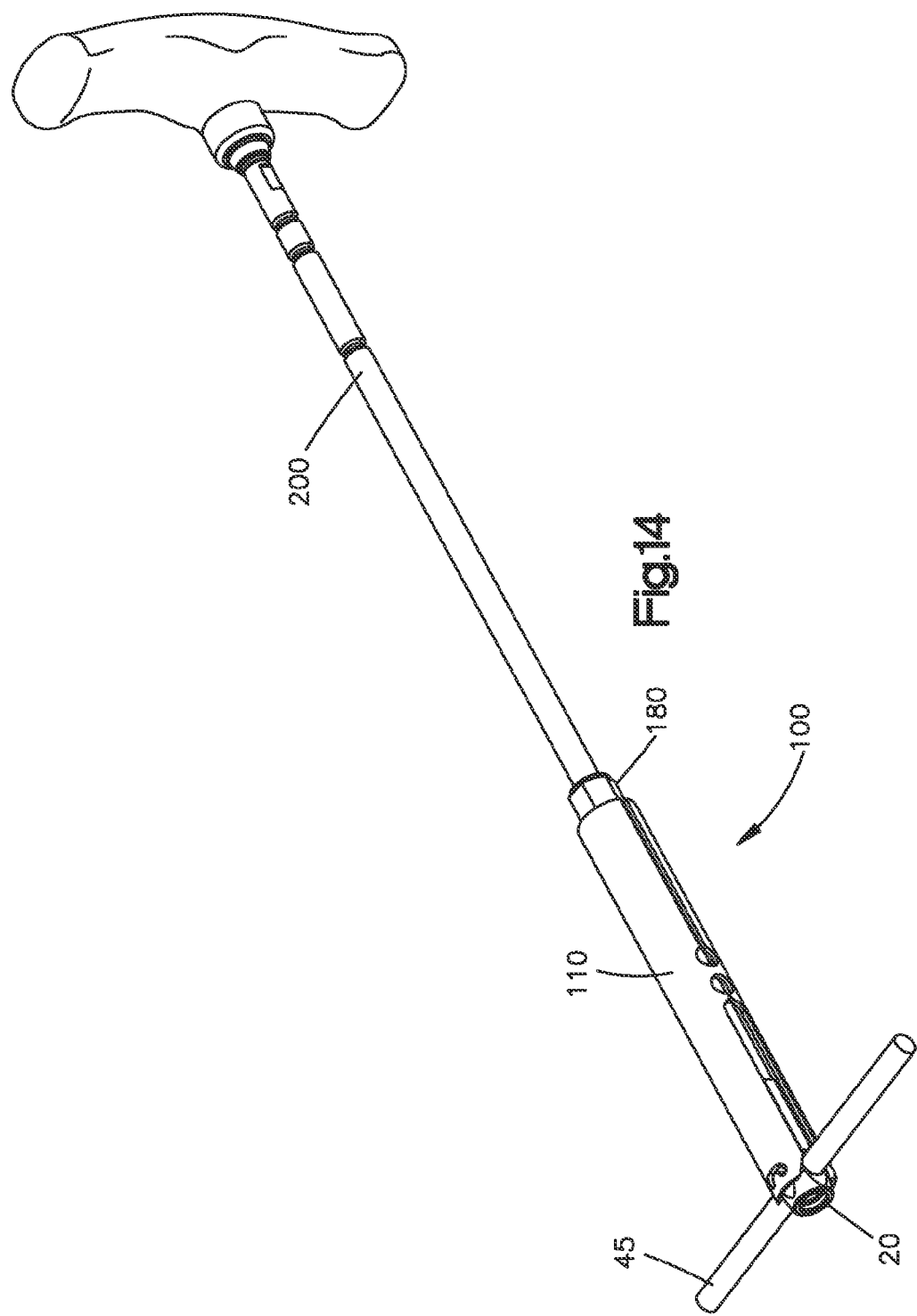
FIG. 14 illustrates a perspective view of the reduction tool shown in FIG. 12 during final securement of the locking cap to the bone fixation element using the driver tool shown in FIG. 13.
Figure 15:
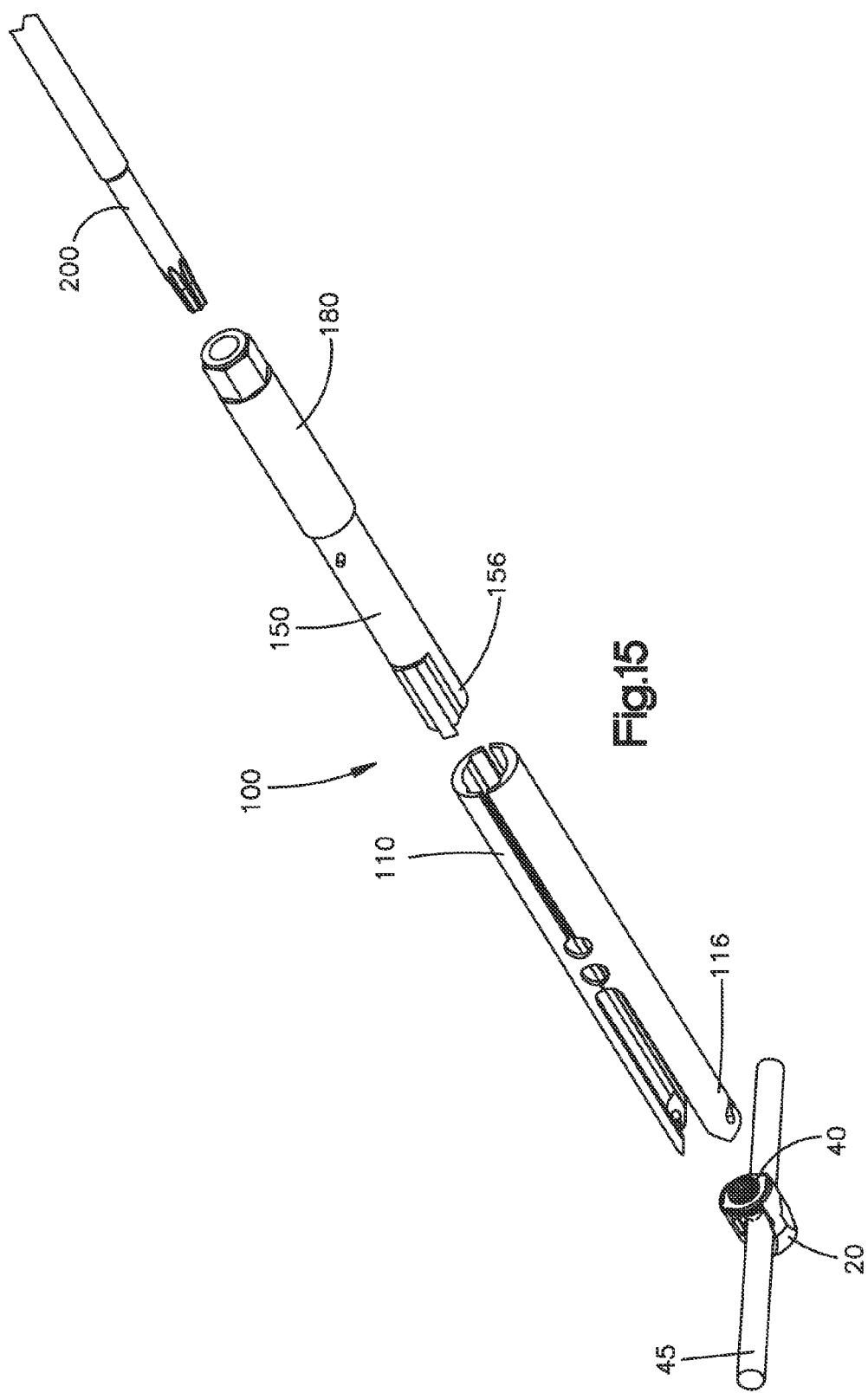
FIG. 15 illustrates an exploded, perspective view of the reduction tool and drive tool shown in FIG. 14 subsequent to final securement of the locking cap to the body portion of the bone fixation element and during removal of the outer tube, inner tube, rotatable sleeve and drive tool.

Referring to FIGS. 3 and 10, the proximal end 154 of the inner tube 150 is operatively coupled to the rotatable sleeve 180. The rotatable sleeve 180 is preferably disposed about the inner tube 150. That is, the inner tube 150 is preferably disposed within a lumen 188 formed in the rotatable sleeve 180, as will be described in greater detail below. More preferably, the inner tube 150 is coupled to the rotatable sleeve 180 such that rotation of the rotatable sleeve 180 about the longitudinal axis 152 of the inner tube 150 does not rotate the inner tube 150. The inner tube 150 does not rotate while the surgeon is rotating the rotatable sleeve 180. The outer surface 151 of the inner tube 150 preferably includes a shoulder or lip 175 formed thereon for reasons described below.

Referring to FIGS. 3 and 10, the rotatable sleeve 180 includes a longitudinal axis 182, a proximal end 184, a distal end 186 and a lumen 188 extending from the proximal end 184 to the distal end 186. The rotatable sleeve 180 preferably also includes an engagement feature 189 disposed adjacent to or at the proximal end 184 thereof to enable the surgeon to impart a rotational force to the rotatable sleeve 180. The engagement feature 189 can be any feature known in the art including but not limited to, an external hex, an internal hex, threads, etc. The distal end 186 of the rotatable sleeve 180 preferably terminates adjacent to and preferably contacts the shoulder or lip 175 formed on the outer surface 151 of the inner tube 150 when the rotatable sleeve 180 is disposed over the outer surface 151 of the inner tube 150. In one embodiment, threading 190 is disposed on the outer surface 181 of the rotatable sleeve 180. The threading 190 preferably extends from the distal end 186 of the rotatable sleeve 180. The threading 190 is sized and configured to engage corresponding threading (not shown) formed on the inner surface, preferably adjacent to the proximal end 114, of the outer tube 110 when the inner tube 150 and the rotatable sleeve 180 are disposed within the lumen 118 formed in the outer tube 110.

Referring to FIGS. 11-15, an exemplary method of using the reduction tool 100 will now be described. An incision is made in the patient as required. Preferably, two or more bone fixation elements 10 are implanted into the patient's vertebrae, as required, through the incision. The distal end 116 of the outer tube 110 is coupled to each of the pre-implanted body portions 20 of the bone fixation elements 10, as previously described. Alternatively, the outer tubes 110 may be coupled to the bone fixation elements 10 prior to the bone fixation elements 10 being implanted into the patient's vertebrae. The distal end 156 of the inner tubes 150 are coupled to the locking caps 40 as previously described. The spinal rod 45 is inserted through the diametrically opposed slots 120 extending from the distal end 116 of the outer tubes 110, transversely to the longitudinal axis 112 of the outer tubes 110. Alternatively, the spinal rod 45 may be inserted through the diametrically opposed slots 120 prior to the locking caps 40 being coupled to the inner tubes 150. The inner tube 150 with the locking cap 40 coupled thereto are then inserted into the lumen 118 formed in the outer tube 110. The inner tube 150 is slidably advanced within the lumen 118 of the outer tube 150 until the external threading 190 formed on the outer surface 181 of the rotatable sleeve 180 engages corresponding threads formed on the inner surface of the outer tube 110, at which point further advancement of the inner tube 150 with respect to the outer tube 110 occurs via a rotational force that is imparted to the rotatable sleeve 180 via, for example, the engagement feature 189 formed at the proximal end 184 of the rotatable sleeve 180.

Advancement of the inner tube 150 with respect to the outer tube 110 resulting from the rotation of the rotatable sleeve 180 causes the distal end 186 of the rotatable sleeve 180 to impart a force to the shoulder or lip 175 formed on the outer surface 151 of the inner tube 150, which in turn, causes non-rotational, advancement of the inner tube 150 with respect to the outer tube 110. This in turn advances the locking cap 40 coupled to the distal end 156 of the inner tube 150 into contact with the spinal rod 45, which in turn, advances the spinal rod 45 into the rod-receiving channel 26 formed in the body portion 20 of the bone fixation element 10. In addition, advancement of the inner tube 150 with respect to the outer tube 110 provisionally couples the locking cap 40 to the body portion 20 of the bone fixation element 10 thereby retaining the spinal rod 45 within the rod-receiving channel 26. Over advancement of the locking cap 40 and the spinal rod 45 with respect to the body portion 20 is prevented by the engagement of the pin 177 extending from the outer surface 151 of the inner tube 150 with the pin stop 148 formed in the outer tube 110.

Final securement of the locking cap 40 to the body portion 20 and securement of the spinal rod 45 within the rod-receiving channel 26 of the bone fixation element 10 may be achieved by a drive tool 200, such as a screw driver, a star drive, a hex drive, etc., inserted through the lumens 188, 158, 118 formed in the rotatable sleeve 180, inner tube 150 and outer tube 110, respectively. Rotation of the drive tool 200 preferably secures the locking cap 40 to the body portion 20 of the bone fixation element 10 as well as decouples the inner tube 150 from the locking cap 40. The drive tool 200 and the inner tube 150 are then removed and the outer tube 110 is decoupled from the body portion 20 by, for example, imparting a force to the proximal end 114 of the outer tube 110 as discussed above. Leaving the spinal rod 45 secured within the rod-receiving channel 26 formed in the bone fixation element 10, which is secured to the patient's bone.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

We claim:

1. A rod-reduction and locking cap advancement tool for reducing an elongated spinal rod into a rod-receiving channel formed in a body portion of a bone fixation element and for engaging a locking cap to the body portion, the tool comprising:

an outer tube including a proximal end, a distal end and a lumen defining an inner surface, the lumen extending from the proximal end to the distal end, the distal end including an engagement feature for engaging the body portion of the bone fixation element, the inner surface including a plurality of threads;

an inner tube including a proximal end, a distal end and a lumen extending from the proximal end to the distal end, the inner tube being slidably disposed within the lumen formed in the outer tube, the distal end of the inner tube including an engagement member for engaging the locking cap; and a rotatable sleeve including a proximal end, a distal end and a lumen extending from the proximal end to the distal end, the rotatable sleeve being rotatably coupled to the proximal end of the inner tube, the sleeve including a plurality of external threads for threadably engaging the threads formed on the inner surface of the outer tube such that rotation of the sleeve advances the inner tube with respect to the outer tube and hence downwardly and non-rotationally forces the locking cap and the elongated spinal rod into engagement with the body portion of the bone fixation element to provisionally lock the locking cap to the body portion of the bone fixation element and thus secure the spinal rod within the rod-receiving channel formed in the body portion of the bone fixation element.

2. The tool of claim 1, wherein the outer tube further comprises:

a pair of diametrically opposed slots extending from the distal end of the outer tube such that when the outer tube is engaged to the body portion of the bone fixation element, the diametrically opposed slots align with the rod-receiving channel formed in the bone fixation element, the diametrically opposed slots being sized and configured to enable the elongated spinal rod to transversely extend therethrough;

a pair of diametrically opposed guide slots extending from the proximal end of the outer tube for receiving one or more pins protruding from an outer surface of the inner tube, the guide slots being substantially aligned with the slots; and a pivot point located longitudinally between each of the diametrically opposed slots extending from the distal end of the outer tube and each of the diametrically opposed guide slots extending from the proximal end of the outer tube so that the distal end of the outer tube can be spread apart to facilitate engagement with the body portion of the bone fixation element.

3. The tool of claim 2, wherein the pivot points are located approximately half way between the proximal end and the distal end of the outer tube.

4. The tool of claim 2, further comprising a pin stop formed in the outer tube for contacting the one or more pins protruding from the outer surface of the inner tube to prevent over advancement of the inner tube with respect to the outer tube.

5. The tool of claim 2, wherein the outer tube further comprises one or more guide recesses formed in the inner surface of the outer tube, the guide recesses extending from the proximal end of the outer tube.

6. The tool of claim 5, wherein the inner tube further comprises one or more protrusions formed on an outer surface thereof, the protrusions being slidably received within the guide recesses.

7. The tool of claim 2, wherein the engagement feature formed on the distal end of the inner tube includes a pair of protrusions formed on an outer surface of the inner tube, the protrusion being spaced apart via a channel, the channel being operatively coupled to an engagement member for coupling the locking cap to the inner tube.

8. The tool of claim 7, wherein the pair of protrusions and the engagement member are slidably received within the one or more guide recesses formed in the inner surface of the outer tube.

9. The tool of claim 1, wherein the rotatable sleeve includes a lumen for receiving at least a portion of the inner tube.

10. The tool of claim 1, wherein the rotatable sleeve is operatively coupled to the inner tube such that rotation of the rotatable sleeve does not rotate the inner tube.

11. The tool of claim 10, wherein the inner tube further comprises a shoulder formed on an outer surface thereof for contacting the distal end of the rotatable sleeve when the rotatable sleeve is disposed over the outer surface of the inner tube.

12. The tool of claim 1, further comprising a drive tool advancable through the lumens formed in the outer tube, the inner tube and the rotatable sleeve so that the drive tool engages the locking cap to secure the locking cap to the body portion of the bone fixation element.

13. The tool of claim 12, wherein the sleeve further comprises a distal instrument engagement feature for imparting rotational force to the sleeve.

14. A method of performing spinal fixation including two or more reduction tools and two or more bone fixation elements for advancing an elongated spinal rod into a rod-receiving channel formed in a body portion of each of the bone fixation elements and for engaging a locking cap to the body portion of each bone fixation element, each of the reduction tools including an outer tube, an inner tube and a rotatable sleeve operatively coupled to the inner tube, the method comprising the steps of:
  (a) forming an incision at a desired location in a patient to access the patient's bones;
  (b) implanting two or more bone fixation elements into the patient's bones through the incision;
  (c) coupling the outer tube of one of the reduction tools to each of the bone fixation elements implanted in step (b);
  (d) inserting the spinal rod transversely through each of the outer tubes;
  (e) coupling one of the locking caps to one of the inner tubes for each of the reduction tools;
  (f) inserting one of the inner tubes with the locking cap coupled thereto into a lumen formed in one of the outer tubes until threads formed on the rotatable sleeves engage corresponding threads formed on the outer tubes; and
  (g) rotating the rotatable sleeves to further advance the inner tubes with respect to the outer tubes until the spinal rod is seated within the rod-receiving channels formed in the body portions of the bone fixation elements and the locking caps engage the body portions of the bone fixation elements.

15. The method of claim 14, wherein the inner tubes are advanced with respect to the outer tubes until a pin extending from the inner tubes contact a pin stop formed in the outer tubes.

16. The method of claim 14, further comprising the step of:
  (h) inserting a drive tool into engagement with the locking caps to further rotate the locking caps with respect to the body portions of the bone fixation elements to secure the locking caps to the body portions, wherein the drive tool is inserted through a lumen formed in each of the reduction tools.

17. The method of claim 16, wherein rotation of the drive tool in step (h) further decouples the inner tubes from the locking caps.

18. The method of claim 14, wherein step (c) requires applying a force to the proximal end of each of the outer tubes to spread apart a distal end of the outer tubes so that the outer tubes can surround and engage the body portions of the bone fixation elements.

* * * * *